United States Patent
Young

(10) Patent No.: US 8,052,679 B2
(45) Date of Patent: *Nov. 8, 2011

(54) ABLATION PROBE WITH ELECTRODE ARRAY AND TISSUE PENETRATING DISTAL TIP ELECTRODE

(75) Inventor: Kimbolt Young, Newtonville, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1118 days.

This patent is subject to a terminal disclaimer.

(21) Appl. No.: 11/742,526

(22) Filed: Apr. 30, 2007

(65) Prior Publication Data
US 2007/0203486 A1 Aug. 30, 2007

Related U.S. Application Data

(63) Continuation of application No. 10/966,677, filed on Oct. 14, 2004, now Pat. No. 7,229,438.

(51) Int. Cl.
*A61B 18/14* (2006.01)
(52) U.S. Cl. .............. 606/41; 607/101; 606/47
(58) Field of Classification Search .......... 606/41, 606/45–50; 607/101, 102
See application file for complete search history.

(56) References Cited

U.S. PATENT DOCUMENTS

| | | | |
|---|---|---|---|
| 3,174,851 A | | 3/1965 | Buehler et al. |
| 3,351,463 A | | 11/1967 | Rozner et al. |
| 3,753,700 A | | 8/1973 | Harrison et al. |
| 5,472,441 A | * | 12/1995 | Edwards et al. ......... 606/41 |
| 5,507,743 A | | 4/1996 | Edwards et al. |
| 5,536,267 A | * | 7/1996 | Edwards et al. ......... 606/41 |
| 5,672,173 A | * | 9/1997 | Gough et al. ......... 606/41 |
| 5,827,276 A | * | 10/1998 | LeVeen et al. ......... 606/41 |
| 5,855,576 A | | 1/1999 | LeVeen et al. |
| 6,090,105 A | | 7/2000 | Zepeda et al. |
| 2004/0158239 A1 | | 8/2004 | Behl et al. |
| 2005/0080409 A1 | | 4/2005 | Young et al. |
| 2005/0107781 A1 | | 5/2005 | Ostrovsky et al. |
| 2006/0217702 A1 | | 9/2006 | Young |

FOREIGN PATENT DOCUMENTS

WO  WO 97/06739 A2  2/1997
WO  WO 2005/037119 A1  4/2005

OTHER PUBLICATIONS

PCT International Search Report for PCT/US2005/034023, Applicant: Boston Scientific Scimed, Inc., Forms PCT/ISA/210 and 220, dated Feb. 22, 2006 (5 pages).
PCT Written Opinion of the International Search Authority for PCT/US2005/034023, Applicant: Boston Scientific Scimed, Inc., Form PCT/ISA/237, dated Feb. 22, 2006 (4 pages).
Communication Pursuant to Article 94(3) EPC for EP Application No. 05820951.1, Applicant: Boston Scientific Limited, EPO Forms 2001 and 2906, dated Jan. 8, 2008 (3 pages).

* cited by examiner

*Primary Examiner* — Michael Peffley
(74) *Attorney, Agent, or Firm* — Vista IP Law Group LLP

(57) ABSTRACT

An ablation device includes a cannula having a distal end and a lumen, an array of electrodes deployable from within the lumen, each of the electrodes having a first configuration when inside the lumen, and a second configuration when unconfined outside the lumen, the electrodes having respective distal ends that point at least partially towards a distal direction when deployed, and an operative electrode secured to the distal end of the cannula. In one embodiment, the operative electrode has a shape that is different from the array of electrodes. In another embodiment, the operative electrode is not retractable within the lumen.

20 Claims, 5 Drawing Sheets

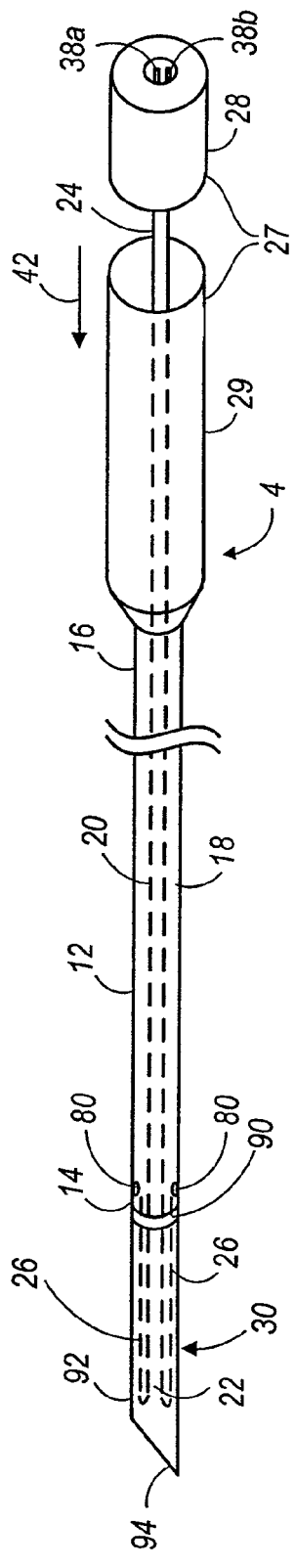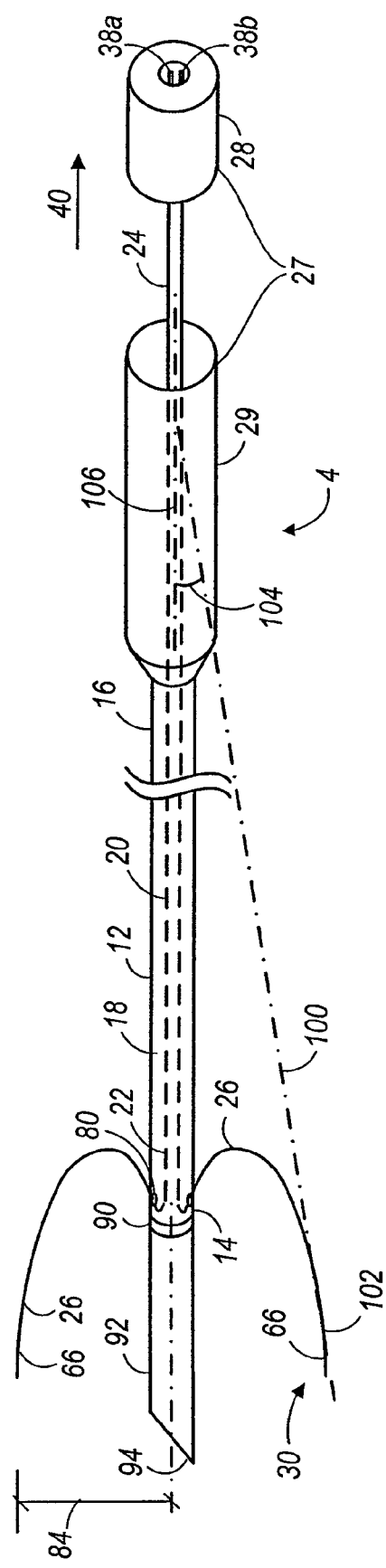

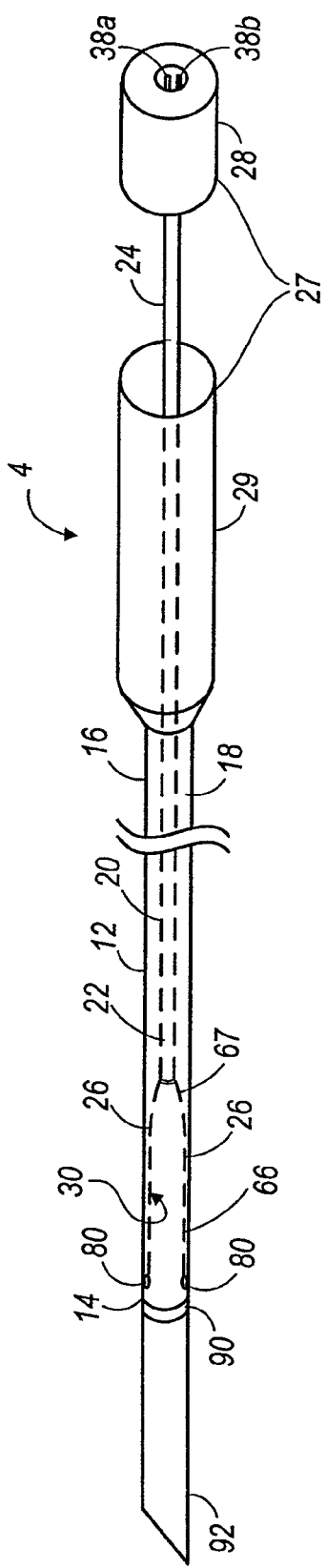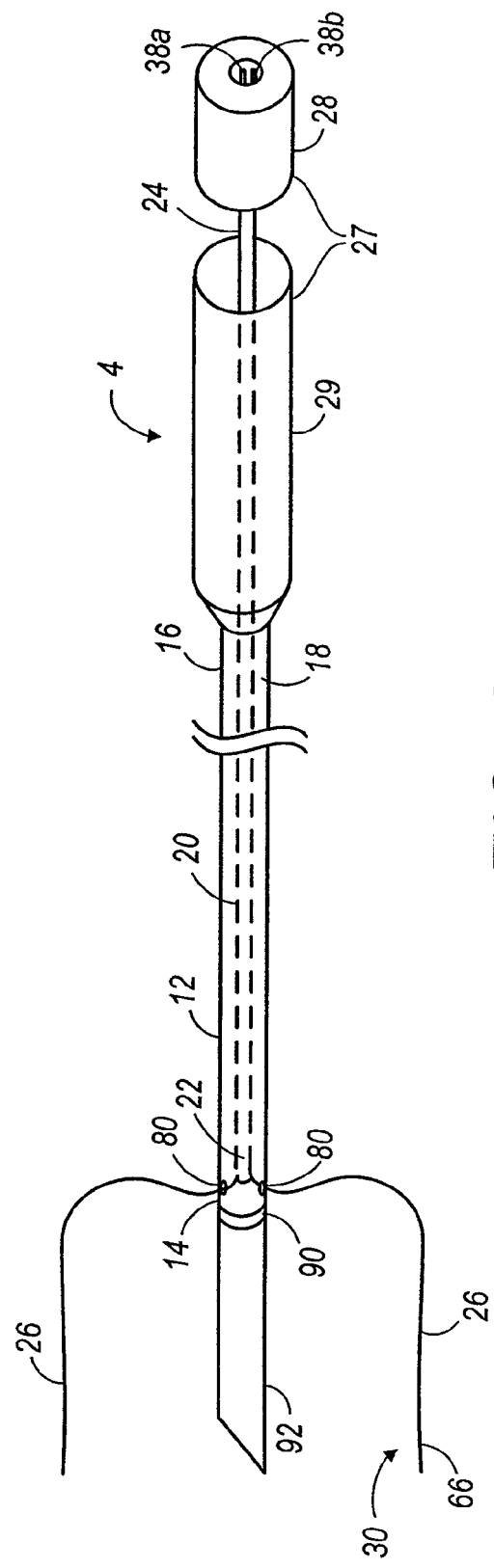
FIG. 5
FIG. 6

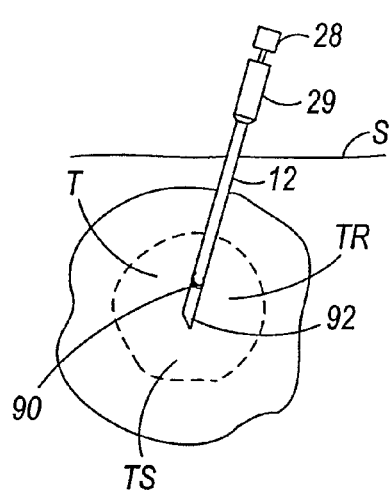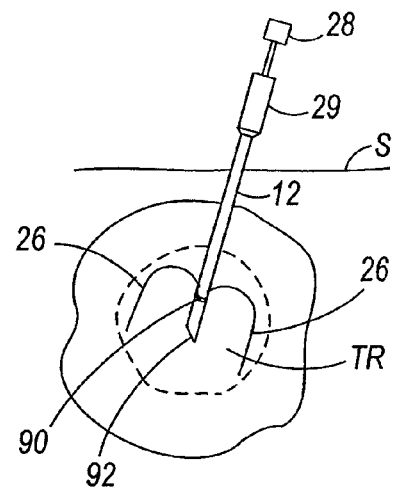
FIG. 7A  FIG. 7B
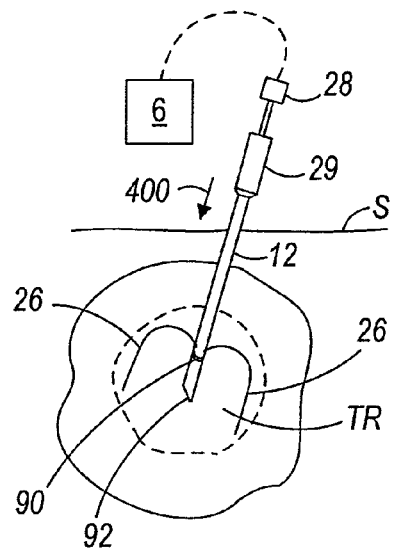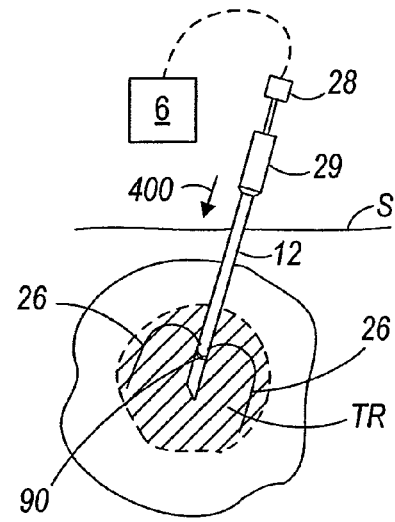
FIG. 7C  FIG. 7D

ABLATION PROBE WITH ELECTRODE ARRAY AND TISSUE PENETRATING DISTAL TIP ELECTRODE

This application is a continuation of U.S. application Ser. No. 10/966,677, filed Oct. 14, 2004, now issued as U.S. Pat. No. 7,229,438, the disclosure of which is hereby incorporated by reference.

FIELD OF THE INVENTION

The field of the invention relates generally to radio frequency (RF) electrosurgical probes for the treatment of tissue, and more particularly, to electrosurgical probes having multiple tissue-penetrating electrodes that are deployed in an array to treat volumes of tissue.

BACKGROUND OF THE INVENTION

Tissue may be destroyed, ablated, or otherwise treated using thermal energy during various therapeutic procedures. Many forms of thermal energy may be imparted to tissue, such as radio frequency electrical energy, microwave electromagnetic energy, laser energy, acoustic energy, or thermal conduction. In particular, radio frequency ablation (RFA) may be used to treat patients with tissue anomalies, such as liver anomalies and many primary cancers, such as cancers of the stomach, bowel, pancreas, kidney and lung. RFA treatment involves destroying undesirable cells by generating heat through agitation caused by the application of alternating electrical current (radio frequency energy) through the tissue.

Various RF ablation devices have been suggested for this purpose. For example, U.S. Pat. No. 5,855,576 describes an ablation apparatus that includes a plurality of electrode tines deployable from a cannula. Each of the tines includes a proximal end that is coupled to a generator, and a distal end that may project from a distal end of the cannula. The tines are arranged in an array with the distal ends located generally radially and uniformly spaced apart from the distal end of the cannula. The tines may be energized in a bipolar mode (i.e., current flows between closely spaced electrode tines) or a monopolar mode (i.e., current flows between one or more electrode tines and a larger, remotely located common electrode) to heat and necrose target tissue within a precisely defined volumetric region of target tissue. To assure that the target tissue is adequately treated and/or to limit damaging adjacent healthy tissues, the array of tines may be arranged uniformly, e.g., substantially evenly and symmetrically spaced-apart so that heat is generated uniformly within the desired target tissue volume.

When using the above described devices in percutaneous interventions, the cannula is generally inserted through a patient's skin, and the tines are deployed out of the distal end of the cannula to penetrate target tissue. Particularly, the tines are deployed such that the distal ends of the tines initially exit from a distal opening at the cannula. As the tines are further deployed, the distal ends of the tines evert radially away from an axis of the cannula, and then back towards a proximal end of the cannula (so that they face substantially in the proximal direction when fully deployed). As such, the tines/electrodes of the above described device each has a profile that resembles a parabola after the electrodes are deployed. The tines are then energized to ablate the target tissue.

Sometimes, a vessel or sensitive tissue may be located at or adjacent to a distal region of a target tissue that is to be ablated. In such cases, use of the above described devices may perforate the blood vessel and/or injure the sensitive tissue. Particularly, deploying the electrodes at the distal end of the cannula such that the deployed electrodes evert proximally towards a proximal end increases the risk that the electrodes will injure the blood vessel or the sensitive tissue as the electrodes are being deployed.

In addition, when using heat to kill tissue at a target site, the effective rate of tissue ablation is highly dependent on how much of the target tissue is heated to a therapeutic level. In certain situations, complete ablation of target tissue that is adjacent a vessel may be difficult or impossible to perform, since significant bloodflow may draw the produced heat away from the vessel wall, resulting in incomplete necrosis of the tissue surrounding the vessel. This phenomenon, which causes the tissue with greater blood flow to be heated less, and the tissue with lesser blood flow to be heated more, is known as the "heat sink" effect. It is believed that the heat sink effect is more pronounced for ablation of tissue adjacent large vessels that are more than 3 millimeters (mm) in diameter. Due to the increased vascularity of the liver, the heat sink effect may cause recurrence of liver tumors after a radio frequency ablation.

Thus, there remains a need to provide for improved ablation devices.

SUMMARY OF THE INVENTION

In accordance with some embodiments, an ablation device includes a cannula having a distal end and a lumen, an array of electrodes deployable from within the lumen, each of the electrodes having a first configuration when inside the lumen, and a second configuration when unconfined outside the lumen, the electrodes having respective distal ends that point at least partially towards a distal direction when deployed, and an operative electrode secured to the distal end of the cannula, the operative electrode having a shape that is different from the array of electrodes.

In accordance with other embodiments, an ablation device includes a cannula having a distal end and a lumen, an array of electrodes deployable from within the lumen, each of the electrodes having a first configuration when inside the lumen, and a second configuration when unconfined outside the lumen, the electrodes having respective distal ends that point at least partially towards a distal direction when deployed, and an operative electrode secured to the distal end of the cannula, the operative electrode not retractable within the lumen.

In accordance with other embodiments, an ablation device includes a cannula having a distal end and a lumen, and only one array of electrodes deployable from within the lumen, each of the electrodes having a first configuration when inside the lumen, and a second configuration when unconfined outside the lumen, the electrodes having respective distal ends that point at least partially towards a distal direction when deployed.

In accordance with other embodiments, a method of ablating tissue includes deploying an array of electrodes such that the electrodes at least partially circumscribe a tissue region, deploying an operative electrode within the tissue region, and using the deployed array of electrodes and the operative electrode to ablate the tissue region. The deployed electrodes have respective distal ends that point at least partially towards a distal direction.

In accordance with other embodiments, a method of ablating tissue includes deploying an array of electrodes within a tissue region such that the array of electrodes span at least a portion of the tissue region, pushing the deployed electrodes distally to compress tissue within the tissue region, and delivering energy to the array of electrodes to ablate the tissue within the tissue region.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention. It should be noted that the figures are not drawn to scale and that elements of similar structures or functions are represented by like reference numerals throughout the figures. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 2 is a perspective view of the ablation probe used in the system of FIG. 1, wherein an electrode array is particularly shown retracted;

FIG. 3 is a perspective view of the ablation probe of FIG. 2, wherein an electrode array is particularly shown deployed;

FIG. 5 is a perspective view of an ablation probe used in the system of FIG. 1 in accordance with other embodiments, wherein an electrode array is particularly shown retracted;

FIG. 6 is a perspective view of the ablation probe of FIG. 5, wherein the electrode array is particularly shown deployed; and FIGS. 7A-7D are cross-sectional views, showing a method for treating tissue, in accordance with some embodiments of the invention.

DETAILED DESCRIPTION OF THE EMBODIMENTS

Figure 1:
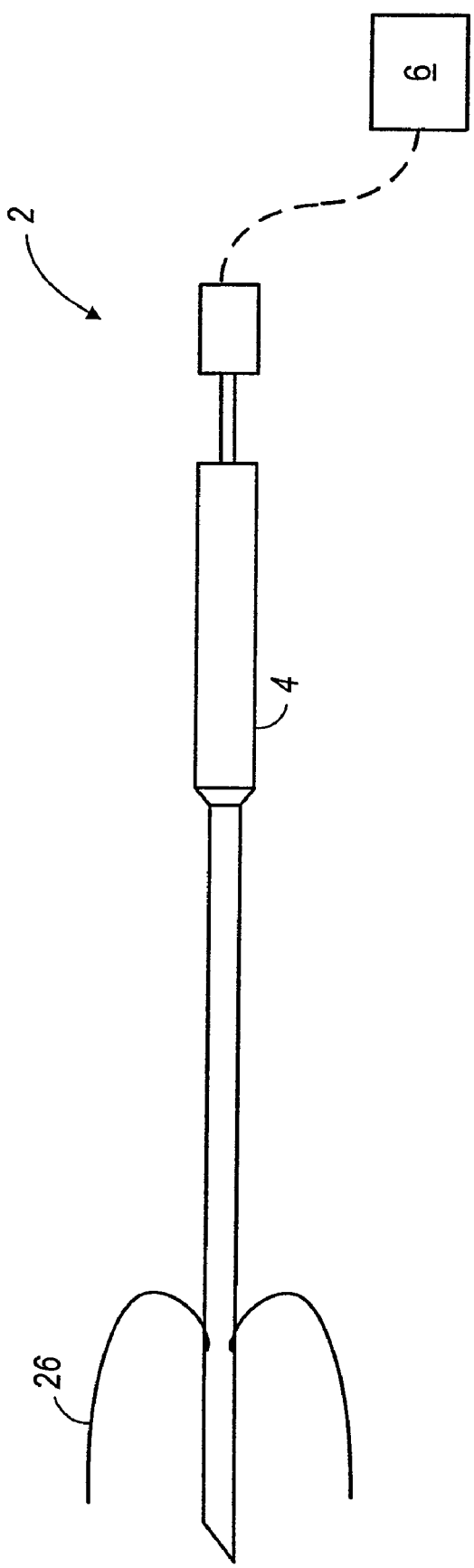
FIG. 1 is a schematic diagram of a tissue ablation system in accordance with some embodiments of the invention.

FIG. 1 illustrates a tissue ablation system 2 constructed in accordance with some embodiments of the invention. The tissue ablation system 2 includes a probe assembly 4 configured for introduction into the body of a patient for ablative treatment of target tissue, and a radio frequency (RF) generator 6 configured for supplying RF energy to the probe assembly 4 in a controlled manner.

Referring specifically now to FIGS. 2 and 3, the probe assembly 4 includes an elongate cannula 12, a shaft 20 slidably disposed within the cannula 12, and an array 30 of electrodes 26 carried by the shaft 20. The cannula 12 has a distal end 14, a proximal end 16, and a central lumen 18 extending through the cannula 12 between the distal end 14 and the proximal end 16. The cannula 12 may be rigid, semi-rigid, or flexible depending upon the designed means for introducing the cannula 12 to the target tissue. The cannula 12 is composed of a suitable material, such as plastic, metal or the like, and has a suitable length, typically in the range from 5 cm to 30 cm, preferably from 10 cm to 20 cm. The length of the cannula 12 can also have other dimensions. If composed of an electrically conductive material, the cannula 12 is preferably covered with an insulative material. The cannula 12 has an outside cross sectional dimension consistent with its intended use, typically being from 0.5 mm to 5 mm, usually from 1.3 mm to 4 mm. The cannula 12 may have an inner cross sectional dimension in the range from 0.3 mm to 4 mm, preferably from 1 mm to 3.5 mm. The cannula 12 can also have other outside and inner cross sectional dimensions in other embodiments.

It can be appreciated that longitudinal translation of the shaft 20 relative to the cannula 12 in a proximal direction 40 deploys the electrode tines 26 from the distal end 14 of the cannula 12 (FIG. 3), and longitudinal translation of the shaft 20 relative to the cannula 12 in a distal direction 42 retracts the electrode tines 26 into the distal end 14 of the cannula 12 (FIG. 2). The shaft 20 comprises a distal end 22 and a proximal end 24. Like the cannula 12, the shaft 20 is composed of a suitable material, such as plastic, metal or the like.

In the illustrated embodiment, each electrode 26 takes the form of an electrode tine, which resembles the shape of a needle or wire. Each of the electrodes 26 is in the form of a small diameter metal element, which can penetrate into tissue as it is advanced from a target site within the target region. In some embodiments, distal ends 66 of the electrodes 26 may be honed or sharpened to facilitate their ability to penetrate tissue. The distal ends 66 of these electrodes 26 may be hardened using conventional heat treatment or other metallurgical processes. They may be partially covered with insulation, although they will be at least partially free from insulation over their distal portions.

When deployed from the cannula 12, the array 30 of electrodes 26 has a deployed configuration that defines a volume having a periphery with a radius 84 in the range from 0.5 to 4 cm. However, in other embodiments, the maximum radius can be other values. The electrodes 26 are resilient and preshaped to assume a desired configuration when advanced into tissue. In the illustrated embodiments, the electrodes 26 diverge radially outwardly from the cannula 12 in a uniform pattern, i.e., with the spacing between adjacent electrodes 26 diverging in a substantially uniform and/or symmetric pattern.

Figure 4A:
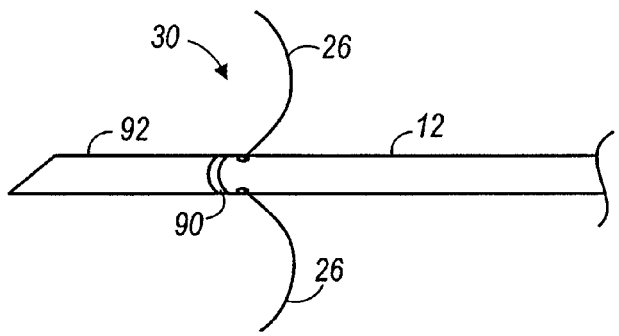
FIG. 4A-4D are side views of ablation probes in accordance with other embodiments of the invention, showing the ablation probes having electrode arrays with different configurations.
Figure 4B:
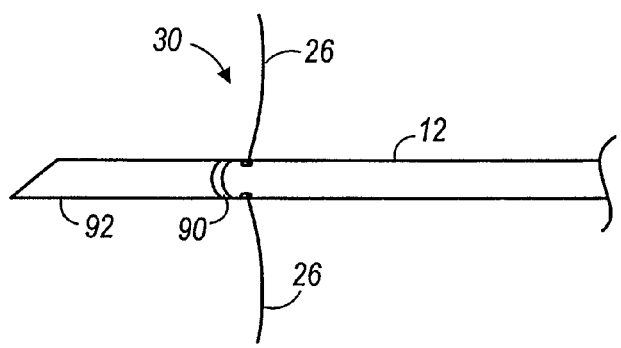
Figure 4C:
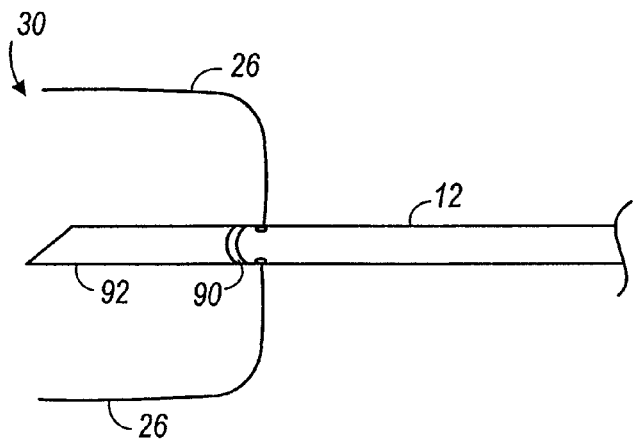
Figure 4D:
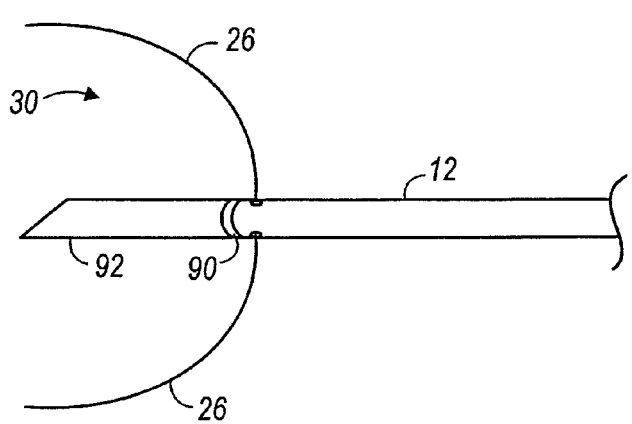

In the illustrated embodiments, each electrode 26 has a flared curvilinear profile that resembles a portion of a parabola. Particularly, when the electrodes 26 are deployed, the electrodes 26 each extends proximally, and then everts distally, such that each electrode 26 forms a profile that resembles at least a portion of a parabola. As shown in FIG. 3, the deployed electrode 26 is located at the distal end 14 of the cannula, and each deployed electrode 26 has a distal end that points at least partially towards a distal direction. Such configuration is advantageous in that it allows the deployed electrodes 26 to be used to compress tissue that is circumscribed by the deployed electrodes 26, thereby reducing blood flow to the tissue and reducing an amount of heat that could be carried away by blood flow. Also, use of the electrodes 26 having the configuration shown in FIG. 3 can prevent or substantially reduce the risk of injury to vessel or sensitive tissue that is adjacent to a distal region of a target area. The distal end 66 of the electrode 26 is considered pointing at least partially towards a distal direction when an instantaneous tangent 100 at a point 102 along the distal end 66 of the electrode 26 forms an angle 104 that is less than 90° with an axis 106 of the cannula 12. It should be noted that the electrodes 26 should not be limited to having the profiles shown in FIG. 3, and that in alternative embodiments, the electrodes 26 can have different deployed profiles. For examples, in other embodiments, the electrodes 26 can each have a flared deployed profile (FIG. 4A), a substantially rectilinear deployed profile (FIG. 4B), a deployed profile that resembles a 90° bent (FIG. 4C), or a deployed profile that resembles a portion (e.g., a quarter) of a circle or an ellipse (FIG. 4D).

It should be noted that although a total of two electrodes 26 are illustrated in FIG. 3, in other embodiments, the probe assembly 4 can have more or fewer than two electrodes 26. In exemplary embodiments, pairs of adjacent electrodes 26 can be spaced from each other in similar or identical, repeated patterns and can be symmetrically positioned about an axis of the shaft 20. It will be appreciated that a wide variety of particular patterns can be provided to uniformly cover the region to be treated. In other embodiments, the electrodes 26 may be spaced from each other in a non-uniform pattern.

The electrodes 26 can be made from a variety of electrically conductive elastic materials. Very desirable materials of construction, from a mechanical point of view, are materials which maintain their shape despite being subjected to high stress. Certain "super-elastic alloys" include nickel/titanium alloys, copper/zinc alloys, or nickel/aluminum alloys. Alloys that may be used are also described in U.S. Pat. Nos. 3,174,851, 3,351,463, and 3,753,700, the disclosures of which are hereby expressly incorporated by reference. The electrodes 26 may also be made from any of a wide variety of stainless steels. The electrodes 26 may also include the Platinum Group metals, especially platinum, rhodium, palladium, rhenium, as well as tungsten, gold, silver, tantalum, and alloys of these metals. These metals are largely biologically inert. They also have significant radiopacity to allow the electrodes 26 to be visualized in-situ, and their alloys may be tailored to accomplish an appropriate blend of flexibility and stiffness. They may be coated onto the electrodes 26 or be mixed with another material used for construction of the electrodes 26.

The electrodes 26 have generally uniform widths and rectangular cross-sections. The rectangular cross-sections make the electrodes 26 stiffer in one direction (e.g., the transverse direction) and more flexible in another direction (e.g., the radial direction). By increasing transverse stiffness, proper circumferential alignment of the electrodes 26 within the lumen 18 of the cannula 12 is enhanced. In other embodiments, the widths of the electrodes 26 may be non-uniform, and the cross-sections of the electrodes 26 may be non-rectangular. Exemplary electrodes will have a width (in the circumferential direction) in the range from 0.2 mm to 0.6 mm, preferably from 0.35 mm to 0.40 mm, and a thickness (in the radial direction) in the range from 0.05 mm to 0.3 mm, preferably from 0.1 mm to 0.2 mm.

In the illustrated embodiments, the probe assembly 4 further includes an electrode 92 secured to the cannula 12. The electrode 92 is operative in conjunction with the array 30 to deliver energy to tissue. The electrodes 26 in the array 30 are positive (or active) electrodes while the operative electrode 92 is a negative (or return) electrode for completing energy path(s). In such cases, energy is directed from the electrodes 26 in the array 30 radially inward towards the electrode 92. Alternatively, the electrode 92 can be active electrode while the electrodes 26 in the array 30 are return electrodes for completing energy path(s), in which cases, energy is directed from the electrode 92 radially outward towards the electrodes 26. In the illustrated embodiments, the operative electrode 92 has a tubular shape, but can have other shapes in alternative embodiments. The operative electrode 92 also has a sharp distal tip 94 for piercing tissue. The operative electrode 92 is secured to the distal end 14 of the cannula 12 such that the distal tip of the operative electrode 92 is distal to the distal end 14. In other embodiments, the operative electrode 92 can be secured to the cannula 12 at a point along a length of the cannula 12. In such case, the distal tip of the cannula 12 can have a sharp profile for piercing tissue.

In the illustrated embodiments, the array 30 of electrodes 26 and the operative electrode 92 are used to deliver RF current in a bipolar fashion, which means that current will pass between the array 30 of electrodes 26 and the operative electrode 92. In a bipolar arrangement, the array 30 and the electrode 92 will be insulated from each other in any region(s) where they would or could be in contact with each other during a power delivery phase. If the cannula 12 is made from an electrically conductive material, an insulator 90 can be provided to electrically insulate the operative electrode 92 from the electrodes 26 in the array 30. In other embodiments, the electrode array 30 can be electrically insulated from the operative electrode 92 by an insulator having other shapes or configurations that is placed at different locations in the probe assembly 4. For example, in other embodiments, the probe assembly 4 can include insulators within the respective openings 80. Alternatively, if the cannula 12 is made from a non-conductive material, the insulator 90 is not needed, and the ablation probe 4 does not include the insulator 90.

Alternatively, the RF current is delivered to the electrode array 30 in a monopolar fashion, which means that current will pass from the electrode array 30, which is configured to concentrate the energy flux in order to have an injurious effect on the surrounding tissue, to a dispersive electrode (not shown), which is located remotely from the electrode array 30 and has a sufficiently large area (typically 130 cm$^2$ for an adult), so that the current density is low and non-injurious to surrounding tissue. In such cases, the electrode assembly 4 does not include the operative electrode 92. The dispersive electrode may be attached externally to the patient, e.g., using a contact pad placed on the patient's flank. In other embodiments, the electrode assembly 4 can include the operative electrode 92 for delivering ablation energy in a monopolar configuration. In such cases, the array 30 of electrodes 26 and the operative electrode 92 are monopolar electrodes, and current will pass from the electrodes 26 and the electrode 92 to the dispersive electrode to thereby deliver ablation energy in a monopolar configuration.

Returning to FIGS. 2 and 3, the probe assembly 4 further includes a handle assembly 27, which includes a handle portion 28 mounted to the proximal end 24 of the shaft 20, and a handle body 29 mounted to the proximal end 16 of the cannula 12. The handle portion 28 is slidably engaged with the handle body 29 (and the cannula 20). The handle portion 28 also includes two electrical connectors 38a, 38b, which allows the probe assembly 4 to be connected to the generator 6 during use. Particularly, the electrical connector 38a is electrically coupled to the electrodes 26, and the electrical connector 38b is electrically coupled to the electrode 92. The electrical connector 38a can be conveniently coupled to the electrodes 26 via the shaft 20 (which will be electrically conductive), although in other embodiments, the connector 38a can be coupled to the electrodes 26 via separate wires (not shown). The handle portion 28 and the handle body 29 can be composed of any suitable rigid material, such as, e.g., metal, plastic, or the like. In other embodiments, if the electrode assembly 4 does not include the electrode 92, then the electrode assembly 4 does not include the connector 38b.

Optionally, a marker (not shown) may be placed on the handle portion 28 and/or on the proximal end 24 of the shaft 20 for indicating a rotational orientation or a position of the handle portion 28 relative to the shaft 20 (and the electrodes 26) during use. In some embodiments, the handle assembly 27 can have an indexing feature. For example, the proximal end 24 of the shaft 20 or the handle portion 28 can have one or more keys that mate with respective slot(s) at the interior surface of the cannula 12 or the handle body 29. Such indexing feature allows circumferential alignment of the shaft 20 (and the array 30) relative to the cannula 12. Angle indexing devices that may be used include those described in U.S. patent application Ser. No. 10/317,796, entitled "Angle Indexer For Medical Devices", the entire disclosure of which is expressly incorporated by reference herein. In other embodiments, the handle portion 28 may also include a locking mechanism (not shown) to temporarily lock against the shaft 20 to provide a more stable indexing. For example, the locking mechanism may include an axially-sliding clutch assembly that is slidable along an axis of the shaft 20 to thereby secure the handle portion 28 against the shaft 20. Other securing devices known in the art may also be used.

Referring back to FIG. 1, the RF generator 6 is electrically connected to the electrical connectors 38a 38b, which may be directly or indirectly (e.g., via a conductor) electrically coupled to the electrode array 30. The RF generator 6 is a conventional RF power supply that operates at a frequency in the range from 200 KHz to 1.25 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for vessel occlusion. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as Boston Scientific Corporation of San Jose, Calif., which markets these power supplies under the trademarks RF2000 (100 W) and RF3000 (200 W).

In alternative embodiments, instead of deploying the electrodes 26 by retracting the shaft 20 proximally relative to the cannula 12, the electrodes 26 can be deployed by advancing the shaft 20 distally relative to the cannula 12. FIG. 5 illustrates a variation of the probe assembly 4, wherein the distal ends 66 of the electrodes 26 point at least partially towards a distal direction (e.g., with the distal ends 66 being distal to the proximal ends 67 of the electrodes 26) when confined within the lumen 18 of the cannula. In such cases, the electrodes 26 can be deployed out of the lumen 18 of the cannula by advancing the shaft 20 distally relative to the cannula 12 (FIG. 6). In the illustrated embodiments, each electrode 26 has a flared curvilinear profile that resembles a portion of a parabola and has a distal end that points at least partially towards a distal direction when deployed. In other embodiments, the electrodes 26 can have different deployed shapes/profiles, as similarly discussed previously.

In alternative embodiments, instead of pushing or pulling the handle portion 28 to advance the electrodes 26, the handle assembly 27 can be configured such that the electrodes 26 can be deployed by rotating the handle portion 28 relative to the handle body 27. For example, the shaft 20 can have a screw-like configuration, which allows the shaft 20 to be distally advanced or proximally retracted by rotation of the shaft 20. In such case, the array 30 of electrodes 26 is rotatably coupled to the distal end 22 of the shaft 20 such that rotation of the shaft 20 does not rotate the electrodes 26, but move them in an approximate longitudinal direction.

Referring now to FIGS. 7A-7D, the operation of the tissue ablation system 2 is described in treating a treatment region TR within tissue T located beneath the skin or an organ surface S of a patient. The cannula 12 is first introduced within the treatment region TR, so that the distal end 14 of the cannula 12 is located at the target site TS, as shown in FIG. 7A. This can be accomplished using any one of a variety of techniques. In some cases, the cannula 12 and shaft 20 may be introduced to the target site TS percutaneously directly through the patient's skin or through an open surgical incision. In this case, the cannula 12 (or the electrode 92) may have a sharpened tip, e.g., in the form of a needle, to facilitate introduction to the target site TS. In such cases, it is desirable that the cannula 12 be sufficiently rigid, i.e., have a sufficient column strength, so that it can be accurately advanced through tissue T. In other cases, the cannula 12 may be introduced using an internal stylet that is subsequently exchanged for the shaft 20 and electrode array 30. In this latter case, the cannula 12 can be relatively flexible, since the initial column strength will be provided by the stylet. More alternatively, a component or element may be provided for introducing the cannula 12 to the target site TS. For example, a conventional sheath and sharpened obturator (stylet) assembly can be used to initially access the tissue T. The assembly can be positioned under ultrasonic or other conventional imaging, with the obturator/stylet then removed to leave an access lumen through the sheath. The cannula 12 and shaft 20 can then be introduced through the sheath lumen, so that the distal end 14 of the cannula 12 advances from the sheath to the target site TS.

After the cannula 12 is properly placed, the electrode array 30 is deployed out of the lumen 18 of the cannula 12, as shown in FIG. 7B. Particularly, the electrode array 30 is fully deployed to span at least a portion of the treatment region TR, as shown in FIG. 7B. Alternatively, the needle electrodes 26 may be only partially deployed or deployed incrementally in stages during a procedure.

Next, the RF generator 6 is then connected to the probe assembly 4 via the electrical connectors 38a 38b, and the RF generator 6 is operated to deliver ablation energy to the needle electrodes 26 either in a monopolar mode or a bipolar mode. While ablation energy is being delivered, pressure can be applied to the handle assembly 27 (in the direction 400 shown), thereby causing the electrodes 26 to compress tissue that is being circumscribed by the deployed electrodes 26 (FIG. 7C). The compression on the tissue reduces blood flow to the tissue, thereby preventing or reducing heat from being carried away by blood flow, which in turn, improves a tissue ablation rate. After a desired amount of ablation energy has been delivered, the treatment region TR is necrosed, thereby creating a lesion on the treatment region TR (FIG. 7D).

In many cases, a single ablation may be sufficient to create a desired lesion. However, if it is desired to perform further ablation to increase the lesion size or to create lesions at different site(s) within the treatment region TR or elsewhere, the needle electrodes 26 may be introduced and deployed at different target site(s), and the same steps discussed previously may be repeated. When a desired lesion at treatment region TR has been created, the needle electrodes 26 are retracted into the lumen 18 of the cannula 12, and the probe assembly 4 is removed from the treatment region TR.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. For example, the array 30 of electrodes 26 can be manufactured as a single component. As such, the "array of electrodes" should not be limited to a plurality of separate electrodes, and includes a single structure (e.g., an electrode) having different conductive portions. Thus, the present invention is intended to cover alternatives, modifications, and equivalents that may fall within the spirit and scope of the present invention as defined by the claims.

What is claimed is:

1. An ablation device, comprising:
   a cannula having a distal end and a lumen;
   an array of electrodes deployable from within the lumen, each of the electrodes having a first configuration when inside the lumen wherein the electrodes have respective distal ends that point towards a proximal direction relative to the distal end of the cannula, and a second configuration when unconfined outside the lumen wherein the electrodes have respective distal ends that point at least partially towards a distal direction relative to the proximal end of the cannula when deployed; and
   an operative electrode secured to the distal end of the cannula, the operative electrode being separate from the array of electrodes and having a sharp, tissue penetrating, distal tip.

2. The ablation device of claim 1, wherein the cannula comprises a body and a plurality of openings on the body, the openings sized for allowing the respective electrodes in the array to be deployed therethrough.

3. The ablation device of claim 1, wherein the operative electrode and the array of electrodes operate in a bipolar configuration.

4. The ablation device of claim 1, wherein each of the electrodes in the array has a deployed profile that resembles at least a portion of a parabola.

5. The ablation device of claim 1, wherein the operative electrode has a tubular shape.

6. The ablation device of claim 1, wherein one of the electrodes in the array is configured to exit from within the lumen at a point along the cannula, and the operative electrode is located distal to the point.

7. The ablation device of claim 1, wherein the deployed electrodes have respective distal portions that are arranged in a circumferential configuration to at least partially define a space between the distal portions, and the operative electrode is located at least partially within the space.

8. The ablation device of claim 1, wherein the cannula is configured for being percutaneously introduced through tissue without the aid of a separate device.

9. The ablation device of claim 1, further comprising an insulator electrically insulating the array of electrodes from the operative electrode.

10. The ablation device of claim 9, wherein the insulator comprises a plurality of insulators disposed within respective openings disposed in the cannula.

11. An ablation device, comprising:
    a cannula having a distal end and a lumen;
    an array of electrodes deployable from within the lumen, each of the electrodes having a first configuration when inside the lumen wherein the electrodes have respective distal ends that point towards a proximal direction relative to the distal end of the cannula, and a second configuration when unconfined outside the lumen wherein the electrodes have respective distal ends that point at least partially towards a distal direction relative to the proximal end of the cannula; and
    an operative electrode secured to the distal end of the cannula, the operative electrode not retractable within the lumen and having a sharp, tissue penetrating, distal tip.

12. The ablation device of claim 11, wherein the cannula comprises a body and a plurality of openings on the body, the openings sized for allowing the respective electrodes in the array to be deployed therethrough.

13. The ablation device of claim 11, wherein the operative electrode and the array of electrodes operate in a bipolar configuration.

14. The ablation device of claim 11, wherein each of the electrodes in the array has a deployed profile that resembles at least a portion of a parabola.

15. The ablation device of claim 11, wherein the operative electrode has a tubular shape.

16. The ablation device of claim 11, wherein one of the electrodes in the array is configured to exit from within the lumen at a point along the cannula, and the operative electrode is located distal to the point.

17. The ablation device of claim 11, wherein the deployed electrodes have respective distal portions that are arranged in a circumferential configuration to at least partially define a space between the distal portions, and the operative electrode is located at least partially within the space.

18. The ablation device of claim 11, wherein the cannula is configured for being percutaneously introduced through tissue without the aid of a separate device.

19. The ablation device of claim 11, further comprising an insulator electrically insulating the array of electrodes from the operative electrode.

20. The ablation device of claim 19, wherein the insulator comprises a plurality of insulators disposed within respective openings disposed in the cannula.

* * * * *